United States Patent [19]

Cavalla

[11] 4,127,663
[45] Nov. 28, 1978

[54] THIAZOLE DERIVATIVES TO TREAT INFLAMMATION

[75] Inventor: John F. Cavalla, Isleworth, England

[73] Assignee: John Wyeth & Brother Limited, Maidenhead, England

[21] Appl. No.: 801,972

[22] Filed: May 31, 1977

[30] Foreign Application Priority Data

Jun. 8, 1976 [GB] United Kingdom ............... 23521/76

[51] Int. Cl.$^2$ ............................................ A61K 31/425
[52] U.S. Cl. .................................................... 424/270
[58] Field of Search ........................................ 424/270

[56] References Cited

PUBLICATIONS

Snyder, J. Invest. Dermatol., 54 – 322–325 (1975).
Chem. Abst., 69, 50681 t (1968).

*Primary Examiner*—Stanley J. Friedman
*Attorney, Agent, or Firm*—Arthur E. Wilfond

[57] ABSTRACT 4-(p-Chlorophenyl)-2-phenyl-5-thiazoleacetic acid and its pharmaceutically acceptable salts are useful as topical anti-inflammatory agents. The compounds can be administered in association with a pharmaceutically acceptable topical carrier.

8 Claims, 1 Drawing Figure

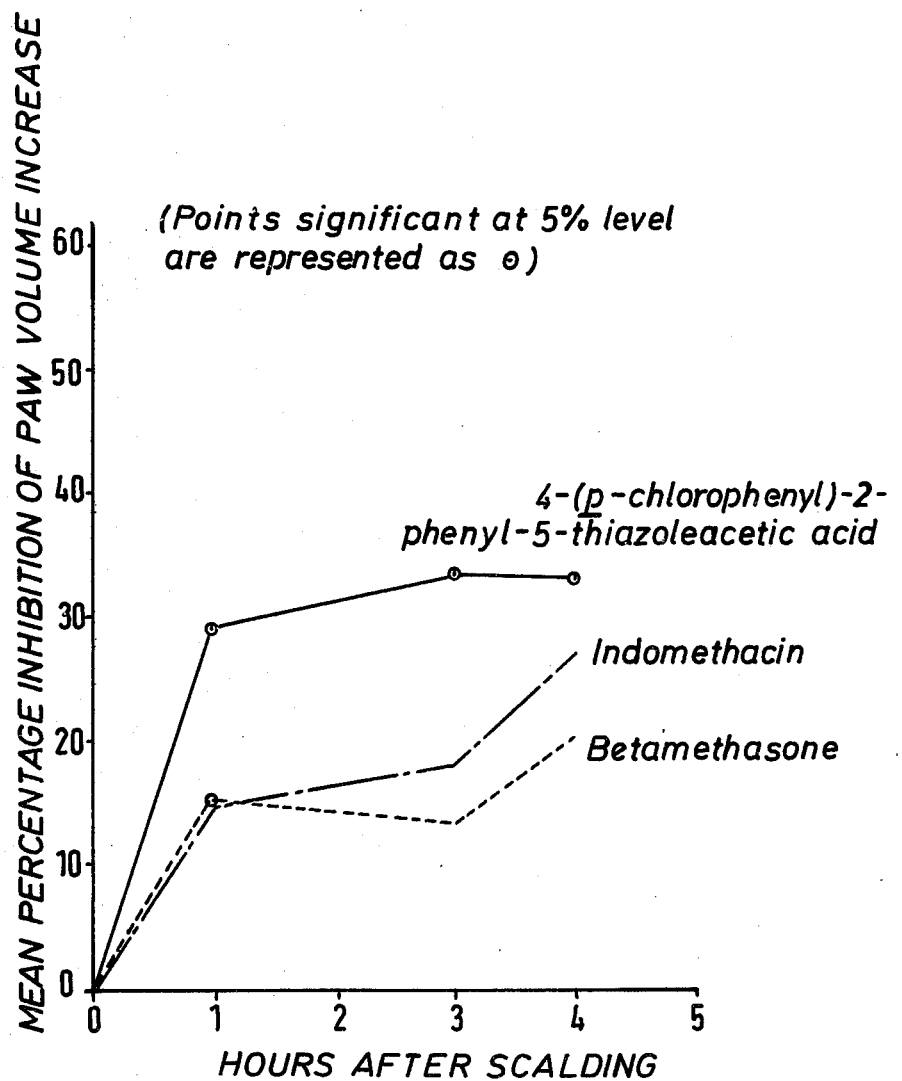

THIAZOLE DERIVATIVES TO TREAT INFLAMMATION

This invention relates to thiazole derivatives. More particularly the invention relates to pharmaceutical compositions for topical use containing certain thiazole derivatives, to methods of preparing such pharmaceutical compositions and to methods for using the thiazole derivatives.

Our U.K. Specification No. 1,145,884 discloses 2,4-diaryl-thiazoles of the general formula

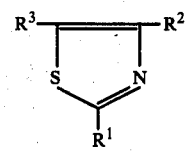

and acid addition salts thereof, in which $R^1$ and $R^2$ are the same or different and are substituted or unsubstituted aryl groups (which may be heteroaryl groups) and $R^3$ is a lower aliphatic carboxylic acid radical containing from 2 to 6 carbon atoms, or a salt, ester, amide, nitrile or hydroxamic acid derivative thereof, said radical $R^3$ being attached to the thiazole ring by a carbon atom of the aliphatic chain.

The prior specification discloses that the thiazoles of general formula I exhibit pharmacological activity, for example anti-inflammatory activity. We have now found that one of the thiazoles, and its pharmaceutically acceptable salts, surprisingly exhibits anti-inflammatory activity upon topical administration.

Accordingly the present invention provides a semi-solid or aerosol pharmaceutical composition for topical administration comprising 4-(p-chlorophenyl)-2-phenyl-5-thiazoleacetic acid or a pharmaceutically acceptable salt thereof in association with a pharmaceutically acceptable topical carrier.

The invention also provides a method of preparing a semi-solid or aerosol composition for topical administration which comprises bringing 4-(p-chlorophenyl)-2-phenyl-5-thiazoleacetic acid or a pharmaceutically acceptable salt thereof into association with a pharmaceutically acceptable topical carrier. The active ingredient may be mixed with the topical carrier.

By 'a semi-solid pharmaceutical composition' is meant an ointment, cream, salve, paste, jelly or other pharamaceutical or cosmetic composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Preferably, the novel compositions of the present invention contain from about 0.1% to about 20% by weight of the active ingredient. The compositions may, for example, contain from about 0.5% (preferably from about 1%) to about 10% by weight of the active ingredient. The active ingredient may be the free acid or a pharamaceutically acceptable salt thereof, for example an alkali metal (e.g. sodium or potassium) or alkali earth metal (e.g. calcium) salt. Preferably the active ingredient is in the free acid form. The active ingredient may be prepared, for example, by the processes described in U.K. Specification No. 1,145,884.

The carrier used in the compositions of the present invention may be any carrier suitable for preparing topical semi-solid compositions or topical aerosol compositions. Examples of suitable carriers for semi-solid compositions are given in Lachman, Lieberman and Kanig (loc-cit) and in Chapter 67 of Remington's Pharmaceutical Sciences, (loc-cit). The carrier for the semi-solid composition may be, for example an emulsion base of the oil in water class (e.g. an emulsion of soft and liquid paraffins in water). Alternatively, the carrier may be an absorption base (e.g. a mixture of wool fat and soft paraffin). A third class of suitable carriers are water miscible bases (e.g. mixtures of high and low molecular weight polyethylene glycols).

When the composition is in aerosol form for topical administration, the composition may comprise the active ingredient and an easily liquidifiable gas. Examples of such liquifiable gases are halogenated hydrocarbons and liquified lower hydrocarbons, both of which are well known as propellants in the aerosol art. (By "lower hydrocarbon" is meant a hydrocarbon containing up to six carbon atoms).

In addition to the active ingredient and the carrier base, the compositions of the invention may contain other ingredients such as antioxidants, buffers, emulsifying agents, perfumes, preservatives and solvents which confer on the product properties desirable in a topical formulation. In particular, buffers may be employed to adjust the pH of the composition to within the range of, for example 4 to 5.5 (e.g. 4.8) to maintain the active ingredient in its free acid form. The composition can also contain active ingredients in addition to 4-(p-chlorophenyl)-2-phenyl-5-thiazoleacetic acid or its salts.

In a further aspect, the invention provides a method of treating inflammation in warm-blooded human and non-human animals which comprises topically administering to the animal an anti-inflammatory effective amount of 4-(p-chlorophenyl)-2-phenyl-5-thiazoleacetic acid or a pharmaceutically acceptable salt thereof. By "topically administering" is meant administering to the exterior skin surface. The active ingredient may be administered in the form of a composition of the present invention.

In one pharmacological experiment demonstrating the anti-inflammatory activity of the thiazole ingredients of the present invention, 4-(p-chlorophenyl)-2-phenyl-5-thiazoleacetic acid was compared with indomethacin and betamethasone. All three compounds were formulated in creams containing an oil in water emulsion base (an emulsion of soft and liquid paraffin in water, stabilized by an emulsifying wax and containing a polyethylene glycol as a solvent). The indomethacin and 4-(p-chlorophenyl)-2-phenyl-5-thiazole acetic acid were used in creams in which their concentration was 1% by weight and the betamethasone creams contained 0.1% by weight. A control cream was also formulated containing the same oil in water emulsion base but no active ingredient. Groups of 6 rats were tattooed on the lateral maleolus of each paw and the paw volumes were determined accurately. The rats were lightly anaesthetised with halothane and then the whole of the hind paw distal to the tattoo marks were immersed for 15 seconds in a water bath maintained at 52.5° C. 30 minutes after immersion the hind paws were massaged with one of the creams (containing an active ingredient or a control cream) for 30 seconds. The paw volumes were then redetermined at intervals of up to 5 hours after immersion. The results for each of the three drugs were pooled and the mean percentage inhibition of paw volume increase for each of the three drugs was calculated and its statistical significance (using Student's t test) determined. The results are given in the accompanying FIGURE. This FIGURE shows that 4-(p-chlorophenyl)-2-phenyl-5-thiazoleacetic acid produced a significant inhibition of heat-induced oedema when administered topically. Indomethacin (1%) and 4-(p-chlorophenyl)-2-phenyl-5-thiazoleacetic acid (1) were more effective than betamethasone (0.1%) but only with 4-(p-chlorophenyl)-2-phenyl-5-thiazole acetic acid was the mean oedema volume in treated animals significantly different from that in controls at all the time points tested.

The following Examples illustrate the invention:

EXAMPLE 1

| Topical formulation containing oil-in-water emulsion base | (a) % w/w | (b) % w/w |
|---|---|---|
| 4-(p-Chlorophenyl)-2-phenyl-5-thiazoleacetic acid | 1.000 | 5.000 |
| Liquid paraffin | 6.000 | 6.000 |
| White soft paraffin | 15.000 | 15.000 |
| Emulsifying wax BP | 9.000 | 9.000 |
| Polyethylene glycol 400 | 33.000 | 33.000 |
| Disodium hydrogen phosphate (anhydrous) | 1.090 | 1.090 |
| Citric acid (monohydrate) | 1.290 | 1.290 |
| Sodium methylhydroxybenzoate | 0.065 | 0.065 |
| Sodium propyl hydroxybenzoate | 0.035 | 0.035 |
| Distilled Water | to 100.000 | 100.000 |

The buffers and preservatives are dissolved in water and mixed well with molten paraffins and emulsifying wax to make a cream. The thiazole derivative is dissolved in hot polyethylene glycol and mixed with molten cream. Water is added to the required amount.

EXAMPLE 2

| Topical formulation containing an absorption base | (a) % w/w | (b) % w/w |
|---|---|---|
| 4-(p-chlorophenyl)-2-phenyl-5-thiazoleacetic acid | 2.0 | 10.0 |
| Wool fat | 10.0 | 10.0 |
| White soft paraffin | to 100.0 | 100.0 |

The wool fat and white soft paraffin are melted together, mixed well and allowed to cool. The thiazole derivative is incorporated gradually into the base.

EXAMPLE 3

| Topical formulation containing a water miscible base | (a) % w/w | (b) % w/w |
|---|---|---|
| 4-(p-chlorophenyl)-2-phenyl-5-thiazoleacetic acid | 0.5 | 4.0 |
| Citric acid monohydrate | 0.2 | 0.2 |
| Polyethylene glycol 300 / Polyethylene glycol 4000 | to 100.0 | 100.0 |

The thiazole derivative and citric acid is dissolved in the polyethylene glycol 300. Molten polyethylene glycol 4000 is added at 60° C. and the mixture stirred until cool.

EXAMPLE 4

| Aerosol formulation | | % by weight |
|---|---|---|
| (i) | Concentrate | |
| | Non-ionic emulsifying wax | 2.0 |
| | Ethanol | 60.0 |
| | 4-(p-chlorophenyl)-2-phenyl-5-thiazoleacetic acid (milled) | 5.5 |
| | Water | 31.0 |
| | Perfume | 1.5 |
| (ii) | Aerosol formulation | |
| | Concentrate | 90% |
| | Propellants dichlorodifluoromethane/dichlorotetrafluoroethane, symmetrical (20:80) | 10% |

(a) The concentrate is filled into a suitable aerosol container, the valve assembly applied with purging or vacuum, and the propellant mixture added through the valve under pressure. (b) In an alternative procedure, the concentrate and propellants are filled cold into a cold aerosol container, the valve crimped into place and the assembly allowed to attain room temperature.

I claim:

1. A semi-solid pharmaceutical composition for topical administration comprising an anti-inflammatory effective amount of 4-(p-chlorophenyl)-2-phenyl-5-thiazoleacetic acid or a pharmaceutically acceptable salt thereof in association with a pharmaceutically acceptable topical carrier.

2. A composition as claimed in claim 1 which contains from about 0.1% to about 20% by weight of the active ingredient.

3. A semi-solid composition as claimed in claim 2 in which the carrier is an oil-in-water emulsion base.

4. A semi-solid composition as claimed in claim 2 in which the carrier is an absorption base.

5. A semi-solid composition as claimed in claim 2 in which the carrier is a water miscible base.

6. An aerosol pharmaceutical composition for topical administration comprising an anti-inflammatory effective amount of 4-(p-chlorophenyl)-2-phenyl-5-thiazoleacetic acid or a pharmaceutically acceptable salt thereof in association with a pharmaceutically acceptable topical carrier.

7. An aerosol composition as claimed in claim 6 in which the carrier is a halogenated hydrocarbon or liquified lower hydrocarbon propellant.

8. A method of treating inflammation in warm-blooded human and non-human animals which comprises topically administering to the animal an anti-inflammatory effective amount of 4-(p-chlorophenyl)-2-phenyl-5-thiazoleacetic acid or a pharmaceutically acceptable salt thereof.

* * * * *